United States Patent
Nicolajsen et al.

(10) Patent No.: US 8,598,348 B2
(45) Date of Patent: Dec. 3, 2013

(54) PURIFICATION OF 1-[2-(2,4-DIMETHYL-PHENYLSULFANYL)PHENYL]PIPERAZINE

(75) Inventors: Henrik Vigan Nicolajsen, Copenhagen (DK); Heidi Lopez de Diego, Naerum (DK); Michael Harold Rock, Hvidovre (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 13/148,088

(22) PCT Filed: Feb. 16, 2010

(86) PCT No.: PCT/DK2010/050039
§ 371 (c)(1),
(2), (4) Date: Sep. 12, 2011

(87) PCT Pub. No.: WO2010/094285
PCT Pub. Date: Aug. 26, 2010

(65) Prior Publication Data
US 2012/0004409 A1    Jan. 5, 2012

Related U.S. Application Data

(60) Provisional application No. 61/207,972, filed on Feb. 17, 2009.

(30) Foreign Application Priority Data

Feb. 17, 2009 (DK) ................................. 2009 00223

(51) Int. Cl.
*C07D 295/027* (2006.01)

(52) U.S. Cl.
USPC .......................................................... 544/395

(58) Field of Classification Search
USPC .......................................................... 544/395
See application file for complete search history.

(56) References Cited

FOREIGN PATENT DOCUMENTS

| GB | 852974 | 11/1960 |
|----|--------|---------|
| GB | 1382536 | 2/1975 |
| WO | WO0329232 A1 | 4/2003 |
| WO | WO 2007/144005 | * 12/2007 |
| WO | WO2007144005 A1 | 12/2007 |
| WO | WO2008113359 | 9/2008 |

OTHER PUBLICATIONS

Vippagunta et al. Advanced Drug Delivery Reviews 2001, 48, pp. 3-26.*
Peterson, ML. et al. (Organic Crystal Engineering Chapter 3, John Wiley & Sons, pp. 67-77, 2010.*
"Summary of Evaluations Performed by the Joint FAO/WHO Expert Committee on Food Additives" (Latest Evaluation: 1998).*
Caira M R: "Crystalline Polymorphism of Organic Compounds" in Topics in Current Chemistry, Springer, Berlin, DE LNKD; vol. 198, pp. 163-208 (Jan. 1, 1998).

* cited by examiner

*Primary Examiner* — Noble Jarrell
*Assistant Examiner* — Valerie Rodriguez-Garcia
(74) *Attorney, Agent, or Firm* — Fish & Richardson P.C.

(57) ABSTRACT

The present invention concerns a process for the manufacture of 1-[2-(2,4-dimethylphenylsulfanyl)phenyl]piperazine.

9 Claims, 6 Drawing Sheets

XRPD of 1-[2-(2,4-dimethylphenylsulfanyl)phenyl]piperazine, HBr, β-form

Fig. 1

XRPD of 1-[2-(2,4-dimethylphenylsulfanyl)phenyl]piperazine, HBr, isopropanol solvate

Fig. 2

TGA and DSC thermograms of 1-[2-(2,4-dimethylphenylsulfanyl)phenyl]piperazine, HBr, isopropanol solvate

Fig. 3

1-[2-(2,4-dimethyl-phenylsulfanyl)-phenyl]-4-(2-piperazin-1-yl-phenyl)-piperazine

Fig. 4

1-[2-(5-chloro-2,4-dimethyl-phenylsulfanyl)phenyl]piperazine

Fig. 5

1-[2-(2,6-dimethylphenylsulfanyl)phenyl]piperazine

Fig. 6

PURIFICATION OF 1-[2-(2,4-DIMETHYL-PHENYLSULFANYL)PHENYL]PIPERAZINE

CROSS REFERENCE TO PRIOR APPLICATIONS

This application is the U.S. National Phase under 35 U.S.C. §371 of International Patent Application No. PCT/DK2010/050039, filed Feb. 16, 2010, and claims the benefit of priority of Danish Patent Application No. PA 200900223, filed Feb. 17, 2009 and U.S. Application No. 61/207,972, filed Feb. 17, 2009. Each of the aforementioned applications is hereby incorporated herein by reference in its entirety. The aforementioned International Application published in English on Aug. 26, 2010 as WO 2010/094285 under PCT Article 21(2).

FIELD OF THE INVENTION

The present invention relates to production and purification of 1-[2-(2,4-dimethylphenylsulfanyl)phenyl]piperazine.

BACKGROUND

The international patent applications published as WO 03/029232 and WO 2007/144005 disclose that the compound 1-[2-(2,4-dimethylphenylsulfanyl)-phenyl]piperazine and salts thereof have affinity to the serotonin transporter and the serotonin receptors 3 and 1A (5-HT$_3$ and 5-HT$_{1A}$). This pharmacological profile makes the use of said compounds in the treatment of affective disorders, such as depression and anxiety, attractive. In fact, the compound is currently subjected to clinical trials in affective disorders.

The manufacture of pharmaceutical products is a highly regulated area with many guidelines and rules concerning quality/purity of active pharmaceutical ingredients (API). It is therefore a requirement that manufacturing routes ensure a high purity of final products, one approach towards this aim is to develop specific purification steps.

Crystallisation and re-crystallisation are well-known ways to provide purified compounds. The examples provided in WO 2007/144005 disclose that 1-[2-(2,4-dimethylphenylsulfanyl)-phenyl]piperazine and salts thereof may be crystallised from solvents such as ethylacetate, ethylacetate/water, water and toluene.

SUMMARY OF THE INVENTION

The present inventors have found that including a step in the synthesis of 1-[2-(2,4-dimethylphenylsulfanyl)-phenyl]piperazine and pharmaceutically acceptable salts thereof in which step 1-[2-(2,4-dimethylphenylsulfanyl)-phenyl]piperazine-HBr isopropanol solvate is prepared from 1-[2-(2,4-dimethylphenylsulfanyl)-phenyl]piperazine-HBr removes or reduces impurities and thus provides purified 1-[2-(2,4-dimethylphenylsulfanyl)-phenyl]piperazine and pharmaceutically acceptable salts thereof, e.g. the β-form of the HBr salt.

Hence, in one embodiment, the invention provides a process for the manufacture of 1-[2-(2,4-dimethylphenylsulfanyl)phenyl]piperazine or a pharmaceutically acceptable salt thereof comprising the step of achieving a solution by dissolving 1-[2-(2,4-dimethylphenylsulfanyl)phenyl]piperazine-HBr salt in a solvent comprising more than 65% (v/v) isopropanol.

In one embodiment, the invention provides a process for the manufacture of 1-[2-(2,4-dimethylphenylsulfanyl)phenyl]piperazine or a pharmaceutically acceptable salt thereof comprising the step of precipitating 1-[2-(2,4-dimethylphenylsulfanyl)phenyl]piperazine-HBr isopropanol solvate from a solvent comprising more than 65% (v/v) isopropanol.

In one embodiment, the invention relates to a process for the manufacture of 1-[2-(2,4-dimethylphenylsulfanyl)phenyl]piperazine or a pharmaceutically acceptable salt thereof comprising the step of dissolving 1-[2-(2,4-dimethylphenylsulfanyl)phenyl]piperazine-HBr isopropanol solvate in a solvent that does not form stable solvates with the compound.

In one embodiment, the invention provides a compound which is 1-[2-(2,4-dimethylphenylsulfanyl)phenyl]piperazine-HBr isopropanol solvate.

DETAILED DESCRIPTION OF THE INVENTION

The present invention relates to a purification step which may be used in the manufacture of 1-[2-(2,4-dimethylphenylsulfanyl)phenyl]piperazine and pharmaceutically acceptable salts thereof. The molecular structure of 1-[2-(2,4-dimethylphenylsulfanyl)-phenyl]piperazine is depicted below In particular, pharmaceutically acceptable salts are acid addition salts of acids that are non-toxic. Said salts include salts made from organic acids, such as maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, theophylline acetic acids, as well as the 8-halotheophyllines, for example 8-bromotheophylline. Said salts may also be made from inorganic salts, such as hydrochloric, hydrobromic, sulfuric, sulfamic, phosphoric and nitric acids. Particular mention is made of salts made from lactic acid, methanesulfonic acid, maleic acid, fumaric acid, meso-tartaric acid, (+)-tartaric acid, (−)-tartaric acid, hydrochloric acid, hydrobromic acid, sulphuric acid, phosphorous acid and nitric acid. Distinct mention is made of the hydrobromide salt.

Figure 1:
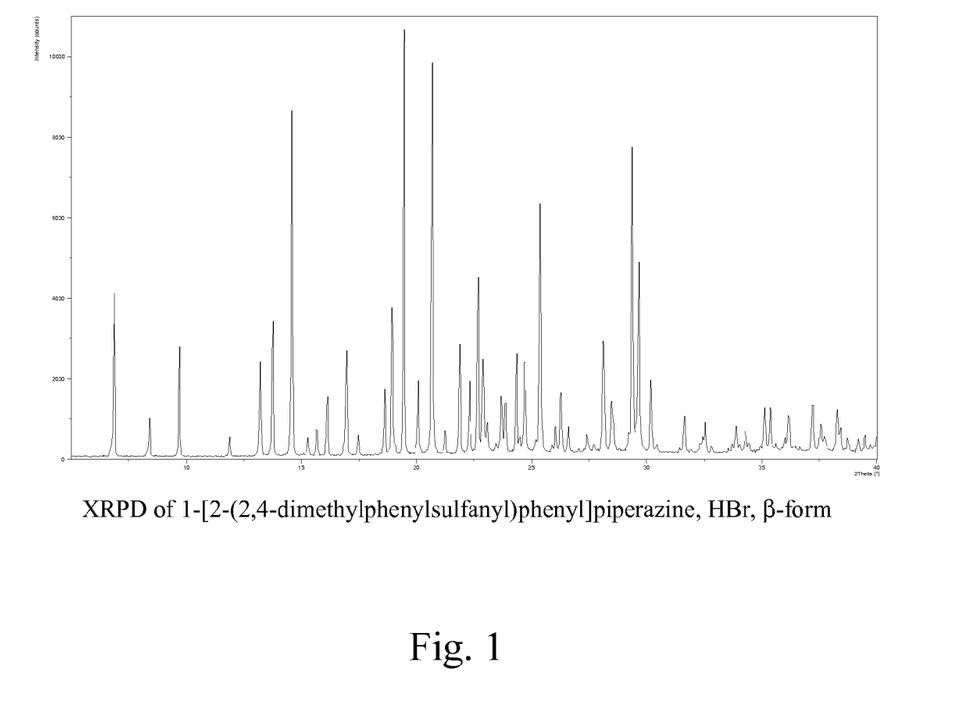
FIG. 1: XRPD of 1-[2-(2,4-dimethylphenylsulfanyl)phenyl]piperazine-HBr, β-form

As shown in WO 2007/144005, HBr salt crystals of 1-[2-(2,4-dimethylphenyl-sulfanyl)phenyl]piperazine are polymorphic and exist in (at least) three different forms, i.e. the α-, the β- and the γ-form—the alpha-, beta- and gamma-form. Judged from DSC and solubility data, the β-form is the most stable form, and it is characterised by XRPD reflections at approximately 6.86, 9.73, 13.78 and 14.62 (° 2θ). An XRPD pattern of the β-form is depicted in FIG. 1. Please see example 1 for the preparation of 1-[2-(2,4-dimethylphenylsulfanyl) phenyl]piperazine-HBr, β-form.

Manufacturing processes for the compound are disclosed in WO 03/029232 and WO 2007/144005. One manufacturing process exploits Buchwald palladium catalysis (see U.S. Pat. No. 5,576,460) to prepare the N-aryl bond. In this process 2,4-dimethylthiophenol, 2-bromo-1-iodobenzene and piperazine are mixed together with a palladium source and a phosphine ligand in a suitable solvent, e.g. toluene, at elevated pH. Other di-halogen benzenes may be used and the piperazine may be protected. Suitable palladium sources include $Pd_2$ $dba_3$, $Pddba_2$ and $Pd(OAc)_2$. dba abbreviates dibenzylideneacetone. Particular mention is made of $Pddba_2$. Suitable phosphine ligands include monodentate and bidentate ligands, such as racemic 2,2'-bis-diphenylphosphanyl-[1,1']binaphtalenyl (rac-BINAP), 1,1'-bis(diphenylphosphino) ferrocene (DPPF), bis-(2-diphenylphosphinophenyl)ether (DPEphos), tri-t-butyl phosphine (Fu's salt), biphenyl-2-yl-di-t-butyl-phosphine, biphenyl-2-yl-dicyclohexyl-phosphine, (2'-dicyclohexylphosphanyl-biphenyl-2-yl)-dimethyl-amine, [2'-(di-t-butyl-phosphanyl)-biphenyl-2-yl]-dimethyl-amine, and dicyclohexyl-(2',4',6'-tri-propyl-biphenyl-2-yl)-phosphane. Moreover, carbene ligands, such as e.g. 1,3-bis-(2,6-di-isopropyl-phenyl)-3H-imidazol-1-ium; chloride may be used in stead of phosphine ligands. In particular, rac-BINAP is a useful ligand. Base is added to the reaction mixture to increase or elevate pH. In particular bases selected from NaO(t-Bu), KO(t-Bu) and $Cs_2CO_3$ are useful. Organic bases, such as 1,8-diazabicyclo[5.4.0]undec-7-ene (DBU) and 1,4-diazabicyclo[2.2.2]octane (DABCO) may be applied as well. Particular mention is made of NaO(t-Bu) and KO(t-Bu).

Alternatively, the thiophenol and the di-halogenbenzene may be reacted in a first step to achieve phenylsulfanylphenyl, which may be isolated before further reaction with piperazine or protected piperazine to achieve the desired product.

In order to obtain a desired salt of 1-[2-(2,4-dimethylphenylsulfanyl)-phenyl]piperazine, the corresponding free base achieved in the above process may be reacted with an appropriate acid to precipitate the salt. In particular, aqueous hydrobromic acid may be used to precipitate 1-[2-(2,4-dimethylphenylsulfanyl)phenyl]piperazine-HBr.

The present invention provides a purification process which can be used e.g. at this step of the manufacturing route. The process provides a highly purified end-product and, moreover, the process allows the use of starting materials of inferior purity. In summary, the HBr salt is dissolved in a solution comprising isopropanol from which solution the corresponding isopropanol solvate is precipitated. It is the experience of the inventors that isopropanol solvates are formed if the solution comprises more than 65% (v/v) isopropanol. The precipitation may be brought about by cooling. The isopropanol solvate is subsequently dissolved in a non-solvate forming solvent, and isopropanol and/or water may be removed or reduced, e.g. by distillation. Removing or reducing isopropanol may be used to increase yield. Finally, 1-[2-(2,4-dimethylphenylsulfanyl)phenyl]piperazine-HBr is precipitated. The choice of solvent and conditions for the precipitation, e.g. temperature ramp, crystal seeding may be used to control the crystal form obtained. The term "non-solvate forming solvent" indicates a solvent, which does not take part in the formation of stable solvates of the 1-[2-(2,4-dimethylphenylsulfanyl)phenyl]piperazine-HBr salt. Examples include water, THF (tetrahydrofuran), xylene, benzene, methanol, ethanol, acetone and toluene, and mixtures hereof. Particular mention is made of toluene mixed with water. Particular mention is made of mixtures comprising more than 80% toluene in water.

Purification by precipitation of corresponding solvates is unusual, and as discussed in Hilfiker, R. (editor). Polymorphism in the Pharmaceutical Industry. Wiley-VCH, 2006. p. 12-13.) such purification step is generally only recommended if the product to be purified is difficult to crystallise in a solvent-free form.

If a salt different from the HBr salt is desired, the purified HBr salt may be used as starting material in further processes in which the HBr salt is dissolved, the free base form is optionally obtained, and the desired salt is achieved by precipitation with an appropriate acid.

In one embodiment, the invention provides a process for the manufacture of 1-[2-(2,4-dimethylphenylsulfanyl)phenyl]piperazine or a pharmaceutically acceptable salt thereof comprising the step of achieving a solution by dissolving 1-[2-(2,4-dimethylphenylsulfanyl)-phenyl]piperazine-HBr salt in a solvent comprising more than 65% (v/v) isopropanol at elevated temperatures, such as reflux temperature. Alternatively, the temperature is not increased, and this will increase process time. In particular, said pharmaceutically acceptable salt is the HBr salt, β-form. In one embodiment, said solvent comprises more than 85% (v/v) isopropanol.

In one embodiment, the invention provides a process for the manufacture of 1-[2-(2,4-dimethylphenylsulfanyl)phenyl]piperazine or a pharmaceutically acceptable salt thereof comprising the step of precipitating 1-[2-(2,4-dimethylphenylsulfanyl)phenyl]piperazine-HBr isopropanol solvate from a solvent comprising more than 65% (v/v) isopropanol, e.g. by cooling. In particular, said pharmaceutically acceptable salt is the HBr salt, β-form. In one embodiment, the solvent comprises more than 85% (v/v) isopropanol.

In one embodiment, the invention provides a process for the manufacture of 1-[2-(2,4-dimethylphenylsulfanyl)phenyl]piperazine or a pharmaceutically acceptable salt thereof comprising the step of dissolving 1-[2-(2,4-dimethylphenylsulfanyl)phenyl]piperazine-HBr isopropanol solvate in a non-solvate forming solvent, followed by precipitation of 1-[2-(2,4-dimethylphenylsulfanyl)phenyl]piperazine-HBr. In particular, said pharmaceutically acceptable salt is the HBr salt, such as the β-form.

In one embodiment, the invention provides a process for the manufacture of 1-[2-(2,4-dimethylphenylsulfanyl)phenyl]piperazine or a pharmaceutically acceptable salt thereof, and in particular the HBr salt, β-form comprising the step of a) achieving a solution by dissolving 1-[2-(2,4-dimethylphenylsulfanyl)phenyl]-piperazine-HBr in a solvent comprising more than 65% (v/v), such as more than 85% (v/v) isopropanol, e.g. at elevated temperatures, such as reflux temperature;

b) precipitating 1-[2-(2,4-dimethylphenylsulfanyl)phenyl]piperazine-HBr, isopropanol solvate from said achieved solution, e.g. by cooling;

c) dissolving 1-[2-(2,4-dimethylphenylsulfanyl)phenyl]piperazine-HBr, isopropanol solvate in a non-solvate forming solvent; in particular, the non-solvate forming solvent comprises more than 80% toluene, such as more than 90%; and d) precipitating 1-[2-(2,4-dimethylphenylsulfanyl)phenyl]piperazine-HBr from the solution obtained in c), e.g. by cooling If the HBr salt used in a) contains a large amount of impurities, it may be beneficial to re-dissolve the isopropanol solvate obtained in b) in a solvent comprising more than 65% isopropanol followed by precipitation as described in b).

In one embodiment, the invention relates to a product directly obtained by one of the processes described above.

In one embodiment, the invention relates to a process of removing or reducing an impurity from solid 1-[2-(2,4-dimethylphenylsulfanyl)phenyl]piperazine-HBr salt or a solution of 1-[2-(2,4-dimethylphenylsulfanyl)phenyl]piperazine-HBr, the process comprising the steps of a) mixing a solvent comprising more than 65% (v/v), such as more than 85% (v/v) isopropanol with solid 1-[2-(2,4-dimethylphenylsulfanyl)phenyl]piperazine-HBr or with a solution of 1-[2-(2,4-dimethylphenylsulfanyl)phenyl]piperazine, HBr as the case may be, e.g. followed by heating as appropriate, to achieve a solution of 1-[2-(2,4-dimethylphenylsulfanyl)phenyl]piperazine-HBr;

b) cooling said achieved solution to precipitate 1-[2-(2,4-dimethylphenylsulfanyl)-phenyl]piperazine-HBr isopropanol solvate;

c) dissolving 1-[2-(2,4-dimethylphenylsulfanyl)phenyl]piperazine-HBr isopropanol solvate in a non-solvate forming solvent; and d) precipitating 1-[2-(2,4-dimethylphenylsulfanyl)phenyl]piperazine-HBr from the solution obtained in c), e.g. by cooling.

In particular, the non-solvate forming solvent used in c) is selected from water, THF, xylene, benzene, methanol, ethanol, acetone and toluene, and mixtures hereof. Particular mention is made of toluene mixed with water, in particular comprising more than 80% (v/v), such as more than 90% (v/v) toluene.

Figure 4:
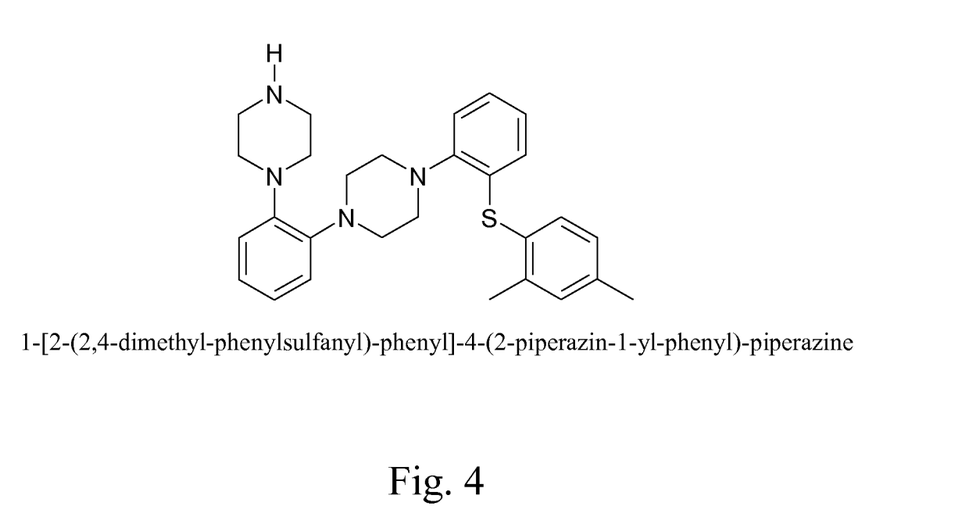
FIG. 4: 1-[2-(2,4-dimethyl-phenylsulfanyl)-phenyl]-4-(2-piperazin-1-yl-phenyl)-piperazine
Figure 5:
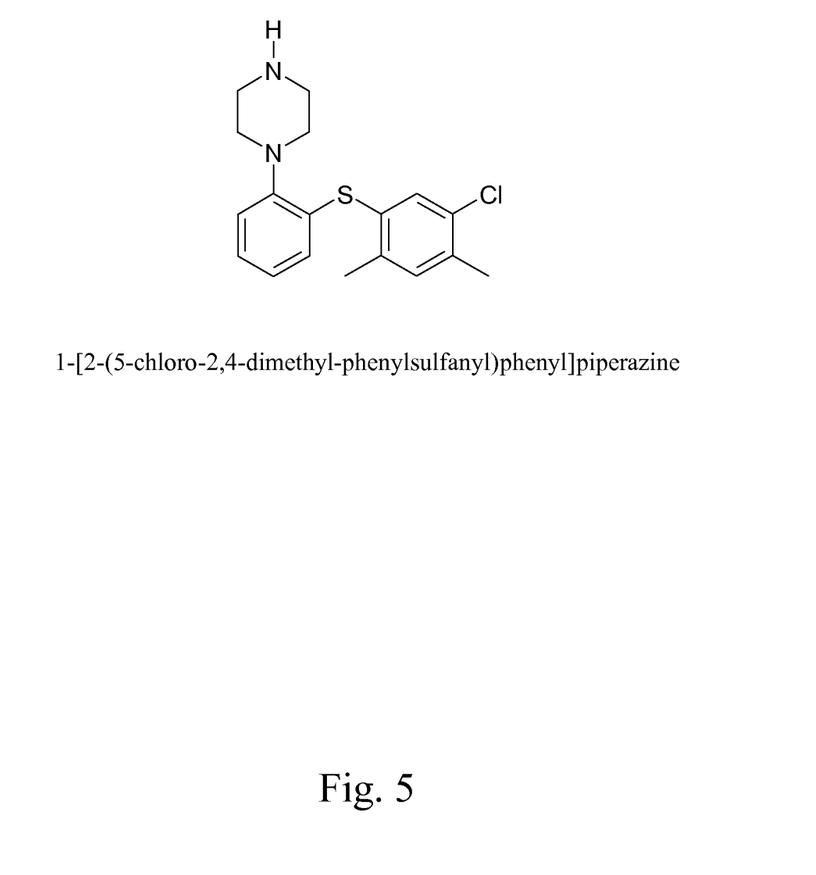
FIG. 5: 1-[2-(5-chloro-2,4-dimethyl-phenylsulfanyl)phenyl]piperazine
Figure 6:
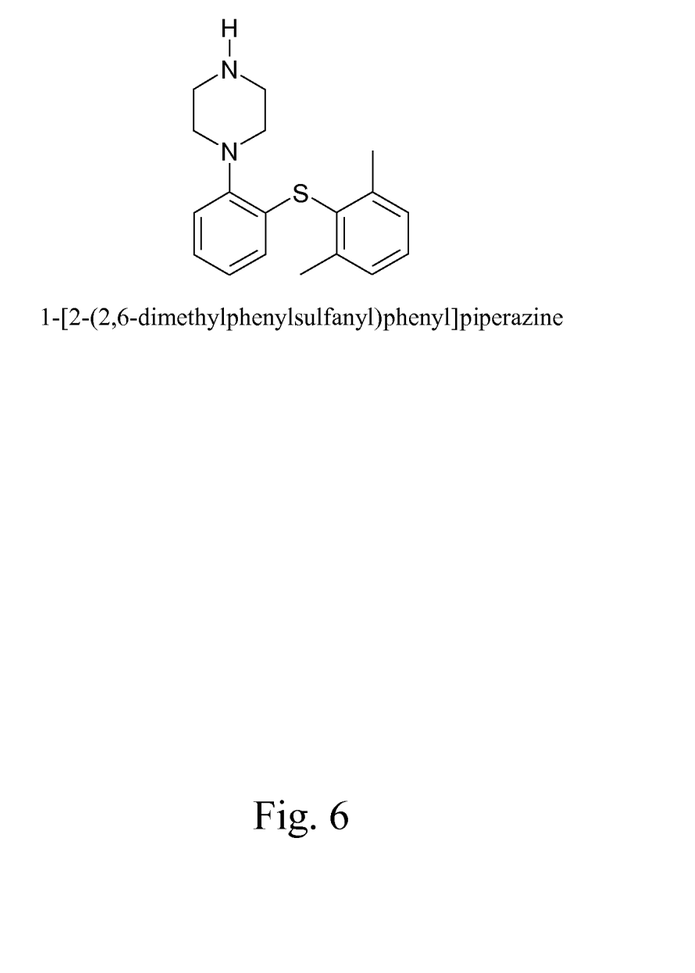
FIG. 6: 1-[2-(2,6-dimethylphenylsulfanyl)phenyl]piperazine

Examples of such impurities include palladium (Pd), 1-[2-(2,4-dimethyl-phenyl-sulfanyl)-phenyl]-4-(2-piperazin-1-yl-phenyl)-piperazine (compound 1), 1-[2-(5-chloro-2,4-dimethyl-phenylsulfanyl)phenyl]piperazine (compound 2), 1-[2-(2,6-dimethylphenylsulfanyl)phenyl]piperazine (compound 3), and 1-[2-(2,4-dimethylphenylsulfanyl)phenyl]piperazine-HBr tert-butanol solvate—see also FIG. 4-6. Palladium is an impurity caused by the use of Pd catalysts. "Pd" or "palladium" is intended to indicate all Pd containing compounds. Compound 1 is an impurity generated when the Pd catalysed N-aryl bond formation takes place at both piperazine nitrogens. Compounds 2 and 3 are impurities carried over from the 2,4-dimethylthiophenol raw material which may be contaminated with the corresponding 5-chloro or 2,5-dimethyl compounds. The tert-butanol solvate may be formed to due to the use of sodium tert-butoxide in the reation.

To further illustrate the invention, the following description may be helpful. 1-[2-(2,4-dimethylphenylsulfanyl)phenyl]piperazine-HBr (A) is charged to a reactor. Isopropanol (10-15 L/kg A) and water (0.3-1.0 L/kg A) is added and agitation is started. The mixture is heated to reflux and all the 1-[2-(2,4-dimethylphenylsulfanyl)phenyl]piperazine, HBr salt is dissolved. The solution is cooled to <20° C., and the crystals (isopropanol solvate) are filtered and washed twice with isopropanol (2.4-2.6 L/kg A, in total). The wet filter cake is recharged to the reactor and toluene (4-6 L/kg A) is added. The isopropanol/water from the wet filter cake is azeotropically distilled off and the toluene lost in the distillation is added together with water (0.2-0.3×A). The mixture is heated to reflux and all the 1-[2-(2,4-dimethylphenylsulfanyl)phenyl]piperazine-HBr is dissolved. The solution is cooled to <20° C., and the crystals are filtered and washed twice with toluene (1.0-4.0 L/kg A, in total). The crystals are dried at elevated temperature, e.g. 60° C. and vacuum. The β-form of the 1-[2-(2,4-dimethylphenylsulfanyl)phenyl]piperazine-HBr is obtained.

As shown in example 5, the purification process of the present invention is superior to equivalent re-crystallisation processes in that more impurities are reduced or removed. Hence, the purification process of the present invention is endowed with unique and unforeseeable qualities.

As illustrated above, 1-[2-(2,4-dimethylphenylsulfanyl)phenyl]piperazine-HBr isopropanol solvate is useful in process steps for the purification of 1-[2-(2,4-dimethylphenylsulfanyl)phenyl]piperazine and pharmaceutically acceptable salts thereof.

Thus, in one embodiment, the invention relates to a liquid solution comprising 1-[2-(2,4-dimethylphenylsulfanyl)phenyl]piperazine in more than 65% (v/v) isopropanol.

In one embodiment, the invention relates to 1-[2-(2,4-dimethylphenylsulfanyl)phenyl]piperazine-HBr isopropanol solvate.

Figure 2:
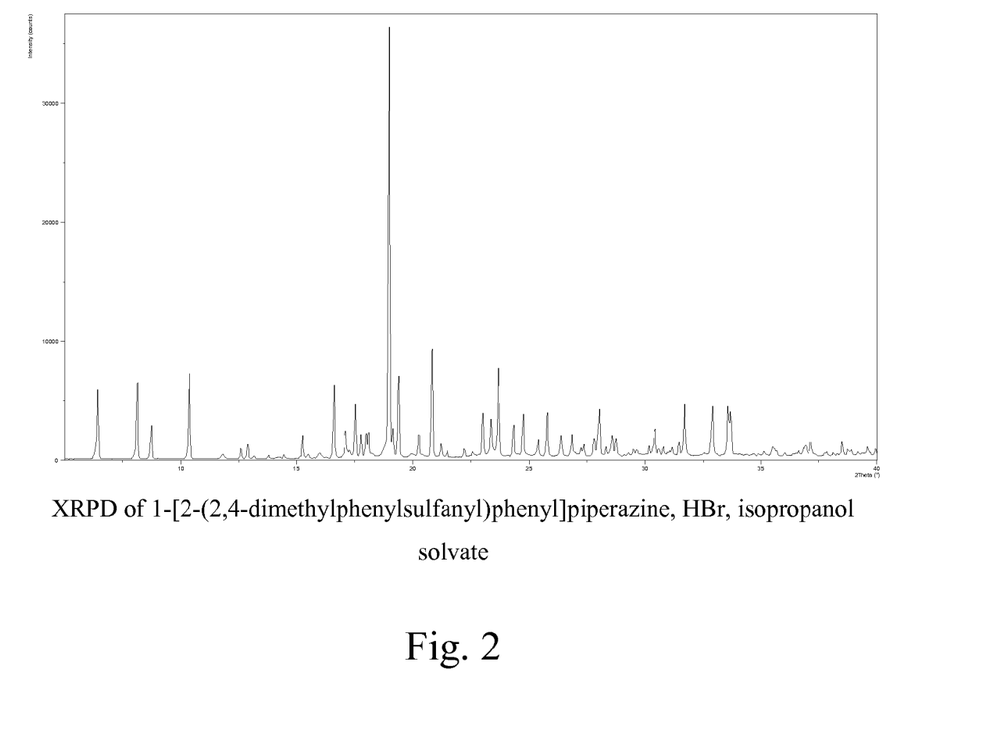
FIG. 2: XRPD of 1-[2-(2,4-dimethylphenylsulfanyl)phenyl]piperazine-HBr, isopropanol solvate

In one embodiment, the invention relates to 1-[2-(2,4-dimethylphenylsulfanyl)phenyl]piperazine-HBr isopropanol solvate with XRPD reflections at approximately 6.44, 8.13, 8.77, 10.41 (° 2θ), e.g. with an XRPD patterns as depicted in FIG. 2.

It is noted that a further benefit of using 1-[2-(2,4-dimethylphenylsulfanyl)phenyl]-piperazine-HBr isopropanol solvate relates to its process properties. The solvate is not static and it is easy to handle on the filters.

All references cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various compounds of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Analytical Methods

$^1$H NMR spectra are recorded at 500.13 MHz on a Bruker Avance DR500 instrument. Dimethyl sulfoxide (99.8% D) is used as solvent, and tetramethylsilane (TMS) is used as internal reference standard.

The melting points are measured using Differential Scanning calorimetry (DSC). The equipment is a TA-Instruments DSC-Q1000 calibrated at 5°/min to give the melting point as onset value. About 2 mg of sample is heated 5°/min in a loosely closed pan under nitrogen flow.

Thermo gravimetric analysis (TGA) used for estimation of solvent/water content of dried material is performed using a TA-instruments TGA-Q500. 1-10 mg sample is heated 10°/min in an open pan under nitrogen flow.

X-Ray powder diffractograms (XRPD) were measured on a PANalytical X'Pert PRO X-Ray Diffractometer using $CuK_{\alpha 1}$ radiation. The samples were measured in reflection mode in the 2θ-range 5-40° using an X'celerator detector. Difraction data are indicated ±0.1 (° 2θ)

The purity of 1-[2-(2,4-dimethylphenylsulfanyl)phenyl]piperazine-HBr was determined using a gradient reverse-phase HPLC method applying a Luna Phenyl hexyl column, 150*4.6 mm, 3 μm particle size. Mobile phases consisted of purified water and acetonitrile acidified with trifluoroacetic acid. Flow rate 1.0 mL/min, column oven 40° C., injection volume 50 μl. Peak areas were quantified with UV detection at 226 nM.

Pd was quantitatively analysed using a Varian Vista PRO ICP-OES (inductively coupled plasma atomic emission spectroscopy). Wavelengths: 340.458 nm, 342.122 nm, 360.955 nm.

Example 1

Preparation of 1-[2-(2,4-dimethylphenylsulfanyl) phenyl]piperazine-HBr, β-Form—See Example 4c of WO 2007/144005

49.5 gram of 1-[2-(2,4-Dimethylphenylsulfanyl)-phenyl] piperazine colourless oil was dissolved in 500 mL ethyl acetate and added 18.5 mL 48%-wt HBr (aq). This addition caused formation of a thick slurry which was stirred over night at room temperature. Filtration and drying in vacuum (50° C.) over night produced the product in 29.6 gram as white solid (47%).

NMR complies with structure. Elemental analysis: 56.86% C, 7.35% N, 6.24% H (Theory for 1:1 salt: 56.99% C, 7.39% N, 6.11% H)

Example 2

Characterization of 1-[2-(2,4-dimethylphenylsulfanyl)phenyl]piperazine-HBr, β-Form—See Example 4d of WO 2007/144005

The beta form of the hydrobromide, as prepared in example 1 is crystalline (XRPD)-see FIG. 1. It has a melting point of ~231° C. It absorbs about 0.6% of water when exposed to high relative humidity and has a solubility of 1.2 mg/mL in water.

Example 3

Preparation of 1-[2-(2,4-dimethylphenylsulfanyl) phenyl]piperazine-HBr, Isopropanol Solvate 1-[2-(2,4-dimethylphenylsulfanyl)phenyl]piperazine-HBr (25 g) was heated in isopropanol (250 mL) resulting in a thick suspension, additional isopropanol (25 mL) and water (25 mL) were added and the suspension was heated to reflux to give a solution. The solution was blank filtered, cooled on an ice bath and filtered. The resultant product was dried under vacuum at 50° C.

Example 4

Figure 3:
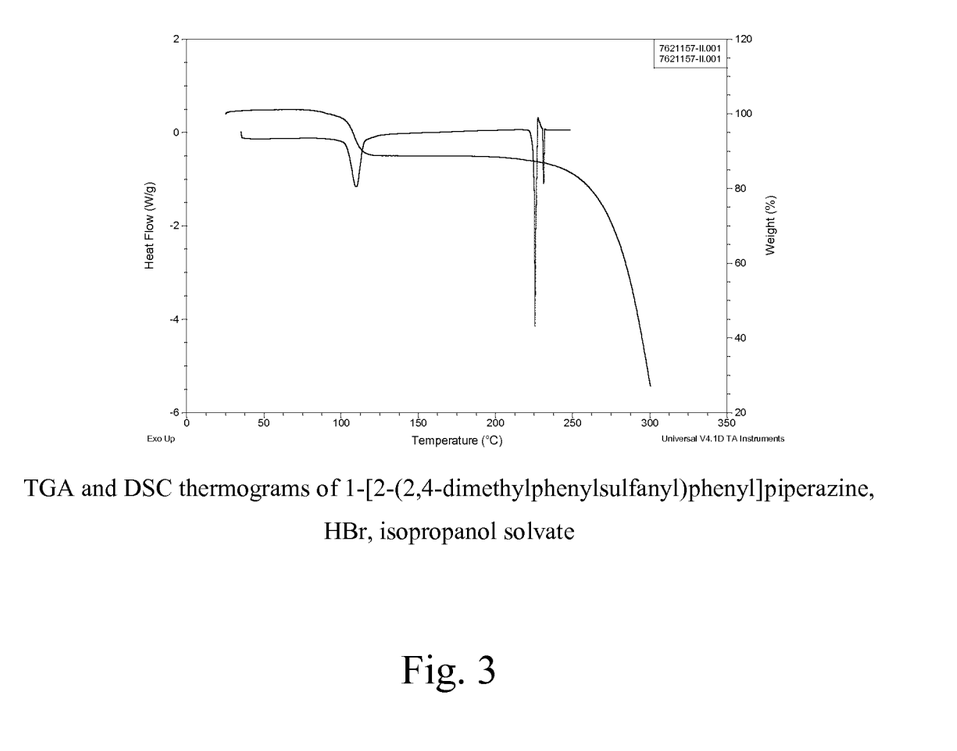
FIG. 3: TGA and DSC thermograms of 1-[2-(2,4-dimethylphenylsulfanyl)phenyl]-piperazine-HBr isopropanol solvate

Characterization of 1-[2-(2,4-dimethylphenylsulfanyl)phenyl]piperazine-HBr Isopropanol Solvate The isopropanol solvate, e.g. as prepared in example 3 is crystalline (XRPD)—see FIG. 2. TGA shows that desolvation starts slowly at 80° C., and the desolvation is complete at 120° C. The weight loss was measured to 12.2%. DSC shows an endotherm corresponding to the desolvation. After desolvation, solvent free crystalline salt is formed which melts at 225° C. This was shown to be the α-form (See WO 2007/144005 for definition of the α-form) by XPRD on a heated sample. The α-form then partly recrystallizes into a form melting at 230° C., probably the β-form. The TGA and DSC thermograms are shown in FIG. 3.

Example 5

Purification of 1-[2-(2,4-dimethylphenylsulfanyl) phenyl]piperazine-HBr

The starting material for both processes in this example was 1-[2-(2,4-dimethylphenylsulfanyl)phenyl]piperazine-HBr containing compound 1 (4.8%), compound 2 (0.19%) and compound 3 (0.18%).

1-[2-(2,4-dimethylphenylsulfanyl)phenyl]piperazine-HBr (33.1 Kg) in a mixture of isopropanol (412 L) and water (18 L) was heated to reflux. The solution was cooled to 20° C. and isopropanol solvate of 1-[2-(2,4-dimethylphenylsulfanyl) phenyl]piperazine was isolated by filtration and washed with isopropanol (82 L). The wet filter cake was dissolved in a mixture of isopropanol (353 L) and water (17 L) at reflux. The solution was cooled to 20° C. and isopropanol solvate of 1-[2-(2,4-dimethylphenylsulfanyl)phenyl]piperazine was isolated by filtration and washed with isopropanol (74 L). The wet filter cake was dissolved in a mixture of toluene (132 L) and water (13 L) at 80° C. and blank filtered. Water and isopropanol were distilled out of the reactor (55 L), distillation was stopped when distillate reached 102° C. Water (7 L) was then added and the solution was cooled to 20° C. slowly. 1-[2-(2,4-dimethylphenylsulfanyl)phenyl]piperazine-HBr was isolated by filtration, filter cake washed with toluene (77 L) and dried. The amounts of impurities were less than 0.05% of compound 1, less than 0.015% of compound 2 and less than 0.05% of compound 3.

For comparison, the starting material was also purified using the following method. 1 g 1-[2-(2,4-dimethylphenyl-sulfanyl)phenyl]piperazine-HBr was heated to reflux in toluene (10 mL). Water (0.6 mL) was then added and the solution was heated to reflux to give a clear solution. This solution was allowed to cool to approximately 20° C. and then further cooled on an ice bath. 1-[2-(2,4-dimethylphenylsulfanyl)phenyl]piperazine-HBr was isolated by filtration and dried in a vacuum oven to give (0.9 g).

The amounts of impurities were 4% of compound 1, 0.15% of compound and 0.14% of compound 3.

Example 6

Purification of 1-[2-(2,4-dimethylphenylsulfanyl) phenyl]piperazine-HBr

The 1-[2-(2,4-dimethylphenylsulfanyl)phenyl]piperazine, HBr batch used in this example contained compound 1 (0.5%).

114 kg of the HBr salt in a mixture of isopropanol (1424 L) and water (64 L) was heated to reflux. The solution was cooled and 1-[2-(2,4-dimethylphenylsulfanyl)phenyl]-piperazine-HBr isopropanol solvate was isolated by filtration. The solvate was dissolved in a mixture of toluene (513 L) and water (50 L) at 80° C. and blank filtered. Water and isopropanol were distilled out, and distillation was stopped when distillate reached 102° C. Water (27 L) was added and the solution was cooled to 20° C. and 1-[2-(2,4-dimethylphenylsulfanyl)phenyl]piperazine-HBr was isolated by filtration. The filter cake was washed with toluene. Analysis of the final product showed less than 0.05% compound 1, and XRDP data confirmed that the β-form was obtained.

Example 7

Manufacture and purification of 1-[2-(2,4-dimethylphenylsulfanyl)phenyl]-piperazine-HBr Under a nitrogen atmosphere Pddba$_2$ (211 mg, 0.367 mmol), BINAP (458 mg, 0.736 mmol), sodium tert-butoxide (26.0 g), piperazine (27.5 g) and toluene (185 mL) were stirred at room temperature for approx 30 minutes. To this mixture was added 1-bromo-2-iodobenzene (12 mL) and 2,4-dimethylthiophenol (12.3 mL) and the reaction mixture was stirred for approximately 60 minutes without heating. The reaction mixture was then heated at reflux for 5 hours, and then water (70 mL) was added followed by stirring for a further 5 minutes before the phases were separated (temperature above 60 C). The toluene phase was washed 2 times with a sodium chloride solution. To the warm toluene phase was added hydrobromic acid 48% (16.2 g), seeding crystals (HBr β-form) were added and the solution was cooled. 1-[2-(2,4-dimethylphenylsulfanyl)phenyl]piperazine-HBr was isolated by filtration, and the filter cake was washed with toluene (160 mL) and water (190 mL). Analysis of a dried sample of filter cake showed 0.64% compound 1 and 70 ppm Pd. The wet filter cake was heated in isopropanol (345 mL) at reflux temperature and the hot solution was blank filtered. The clear solution was cooled to below room temperature, isopropanol solvate of 1-(2,4-dimethylphenylsulfanyl)phenyl]piperazine-HBr was isolated by filtration, washed with isopropanol (40 mL) and dried under vacuum at 40° C. Analysis showed compound 1 (0.05%) and 2 ppm Pd.

1-[2-(2,4-dimethylphenylsulfanyl)phenyl]piperazine-HBr isopropanol solvate (19.5 g), toluene (100 mL) and water (5 mL) were heated to reflux temperature, and water and isopropanol were removed by distillation (23 mL). Toluene was added (23 mL) and the temperature increased to reflux temperature, whereafter water (10 mL) was added and the solution allowed to cool to room temperature. 1-(2,4-dimethylphenylsulfanyl)phenyl]-piperazine-HBr was isolated by filtration, washed with cooled toluene (70 mL) and dried at 50° C. under vacuum. Analysis showed compound 1 under 0.05%, and 1 ppm Pd. XRDP data confirmed that the β-form was obtained.

Example 8

Manufacture and Purification of 1-[2-(2,4-dimethylphenylsulfanyl)phenyl]-piperazine-HBr 1000 g of Pddba$_2$, 3600-4600 g of BINAP, 270-310 kg sodium-tert-butoxide, 360-420 kg piperazine and 1300-1500 L toluene are charged to a reactor, and the mixture is stirred for at least 30 minutes. 210-214 kg 1-Br-2-iodobenzen and 99.5-100.5 kg 2,4-dimethylthiophenol are added and the resulting mixture is stirred for at least 60 min below 25° C. The temperature is increased to 80-95° C. for at least 13 hours. The mixture is cooled, 1000-1200 L water is added and the phases are separated. The toluene phase is washed several times with at a total of 1070-1140 kg ~15% NaCl. 126-128 kg HBr 48% and 40-46 L water are added and the mixture is heated until completely clear solution is obtained. Crude crystals of the title compound are obtained by cooling. The crystals are isolated by filtering, and the crystals are washed with 1000-1200 L toluene and with 400-700 L water. The filter cake is dissolved in 3063-3112 L isopropanol and the solution obtained is blank filtered. The solution is heated and 2470-2964 L is distilled off followed by the addition of 1457-1507 L isopropanol. Complete dissolution is obtained by heating, and crystals of the isopropanol solvate are obtained by cooling. The crystals are isolated by filtering followed by wash with 865-914 L isopropanol.

Add 200 kg of 1-[2-(2,4-dimethylphenylsulfanyl)phenyl]piperazine-HBr isopropanol solvate to 980-1020 L toluene and 48-52 L water. The crystals are dissolved heating and the solution is blank filtered. The solution is distilled until the vapour temperature is above 102° C., and toluene is added in an amount equal to the volume of the distillate. An additional 48-52 L water is added and the liquid is heated until complete dissolution. Crystallisation of 1-[2-(2,4-dimethylphenylsulfanyl)phenyl]piperazine-HBr β form is obtained by cooling and seeding.

The invention claimed is:

1. A process comprising dissolving 1-[2-(2,4-dimethylphenylsulfanyl)phenyl]piperazine-HBr salt in a solvent comprising more than 65% (v/v) isopropanol, to form a 1-[2-(2,4-dimethylphenylsulfanyl)phenyl]piperazine-HBr solvate.

2. A process comprising dissolving 1-[2-(2,4-dimethylphenylsulfanyl)phenyl]piperazine-HBr salt in a solvent comprising more than 65% (v/v) isopropanol to form a 1-[2-(2,4-dimethylphenylsulfanyl)phenyl]piperazine-HBr isopropanol solvate and precipitating said solvate.

3. The process according to claim 2, further comprising removing said isopropanol from said solvate and forming the 1-[2-(2,4-dimethylphenylsulfanyl)phenyl]piperazine HBr salt.

4. The process according to claim 3, wherein said 1-[2-(2,4-dimethylphenylsulfanyl)phenyl]piperazine HBr salt is the β-form.

5. The process according to claim 2, wherein said solvent comprises more than 85% (v/v) isopropanol.

6. A liquid solution comprising 1-[2-(2,4-dimethyl-phenylsulfanyl)-phenyl]-4-(2-piperazin-1-yl-phenyl)-piperazine in more than 65% (v/v) isopropanol.

7. A compound which is 1-[2-(2,4-dimethylphenylsulfanyl)phenyl]piperazine-HBr isopropanol solvate.

8. The compound according to claim 7, which compound has XRPD reflections at approximately 6.44, 8.13, 8.77, 10.41 (° 2θ).

9. The compound according to claim 8 having an XRPD as depicted in FIG. 2.

* * * * *

UNITED STATES PATENT AND TRADEMARK OFFICE
CERTIFICATE OF CORRECTION

PATENT NO. : 8,598,348 B2
APPLICATION NO. : 13/148088
DATED : December 3, 2013
INVENTOR(S) : Henrik Vigan Nicolajsen, Heidi Lopez de Diego and Michael Harold Rock It is certified that error appears in the above-identified patent and that said Letters Patent is hereby corrected as shown below:

In the Specification

Column 3, line 18, delete "$Pd_2$ $dba_3$," and insert -- $Pd_2dba_3$, -- therefor.

Column 3, line 22, delete "binaphtalenyl" and insert -- binaphthalenyl -- therefor.

Column 3, line 31, delete "in stead" and insert -- instead -- therefor.

Column 5, line 50, delete "reation." and insert -- reaction. -- therefor.

Column 6, line 65, delete "DR500" and insert -- DRX500 -- therefor.

Column 7, line 2, delete "calorimetry" and insert -- Calorimetry -- therefor.

Column 7, line 14, delete "Difraction" and insert -- Diffraction -- therefor.

Column 7, line 15, delete "(° 2θ)" and insert -- (° 2θ). -- therefor.

Column 7, line 22, delete "50 μl." And insert -- 50 μL. -- therefor.

Column 7, lines 39-40, delete "over night" and insert -- overnight -- therefor.

Column 7, line 41, delete "over night" and insert -- overnight -- therefor.

Column 10, line 29, delete "β form" and insert -- β-form -- therefor.

In the Claims

Column 10, lines 52-54, in Claim 6, delete
"1-[2-(2,4-dimethyl-phenylsulfanyl)-phenyl]-4-(2-piperazin-1-yl-phenyl)-piperazine" and insert
-- 1-[2-(2,4-dimethyl-phenylsulfanyl)-phenyl]piperazine -- therefor.

Signed and Sealed this
Sixth Day of May, 2014

Michelle K. Lee
*Deputy Director of the United States Patent and Trademark Office*